United States Patent
Mastrodonato

(10) Patent No.: US 11,166,893 B2
(45) Date of Patent: Nov. 9, 2021

(54) TOPICAL HIRSUTISM TREATMENT

(71) Applicant: BMG PHARMA SRL, Milan (IT)

(72) Inventor: Marco Lucio Mastrodonato, Milan (IT)

(73) Assignee: BMG PHARMA S.P.A., Milan (IT)

( * ) Notice: Subject to any disclaimer, the term of this patent is extended or adjusted under 35 U.S.C. 154(b) by 0 days.

(21) Appl. No.: 16/254,665

(22) Filed: Jan. 23, 2019

(65) Prior Publication Data

US 2019/0151217 A1    May 23, 2019

Related U.S. Application Data

(62) Division of application No. 15/759,835, filed as application No. PCT/IB2016/001306 on Sep. 16, 2016, now abandoned.

(30) Foreign Application Priority Data

Sep. 17, 2015   (IT) .................. 102015000052641

(51) Int. Cl.
    A61K 8/41      (2006.01)
    A61K 8/44      (2006.01)
    A61Q 7/02      (2006.01)
    A61K 8/9794    (2017.01)
    A61K 8/9789    (2017.01)

(52) U.S. Cl.
    CPC ............ *A61K 8/41* (2013.01); *A61K 8/44* (2013.01); *A61K 8/9789* (2017.08); *A61K 8/9794* (2017.08); *A61Q 7/02* (2013.01)

(58) Field of Classification Search
    None
    See application file for complete search history.

(56) References Cited

U.S. PATENT DOCUMENTS

| | | | |
|---|---|---|---|
| 7,252,831 B2 * | 8/2007 | Khaiat | ............... A61K 8/9789 424/401 |
| 2007/0059264 A1 | 3/2007 | Ahluwalia et al. | |
| 2011/0117218 A1 | 5/2011 | Schmidt | |
| 2014/0044814 A1 | 2/2014 | Brown | |

FOREIGN PATENT DOCUMENTS

| | | |
|---|---|---|
| CN | 103655408 A | 3/2014 |
| EP | 1074240 A2 | 2/2001 |
| EP | 1844786 A1 | 10/2007 |
| WO | 2005067953 A1 | 7/2005 |

OTHER PUBLICATIONS

Merriam-Webster definition of "superfluous"; https://www.merriam-webster.com/dictionary/superfluous—accessed Nov. 12, 2020.*
Search Report and Written Opinion of PCT/IB2016/001306 dated Jan. 27, 2017.

* cited by examiner

*Primary Examiner* — Susan Hoffman
(74) *Attorney, Agent, or Firm* — Silvia Salvadori, P.C.; Silvia Salvadori

(57) ABSTRACT

Disclosed is a topical composition for the treatment of hirsutism comprising capryloyl glycine as active ingredient, mixed with dermatologically acceptable carriers.

8 Claims, No Drawings

TOPICAL HIRSUTISM TREATMENT

This U.S. non-provisional application is a Divisional of U.S. application Ser. No. 15/759,835 filed on Mar. 14, 2018, now abandoned, which is a U.S. National stage of PCT/IB2016/001306 filed on 16 Sep. 2016, which claims priority to and the benefit of Italian Application No. 102015000052641 filed on 17 Sep. 2015, the contents of which are incorporated herein by reference in their entireties.

The present invention relates to dermatological compositions designed to inhibit the growth of unwanted hair, in particular on women's faces.

PRIOR ART

"Hirsutism" is defined as hair growth in parts of the female body wherein it is normally absent. Said condition can have a number of causes which, in addition to genetic predispositions, include endocrine tumours, polycystic ovary syndrome, congenital adrenal hyperplasia, and use of medicaments such as corticosteroids, progestogens, minoxidil, diazoxide and phenytoin.

Women suffering from this problem, which involves obvious aesthetic and psychological problems, mainly use conventional depilation methods such as hot or cold depilatory waxes, bleaching creams, depilatory creams, mechanical removal by shaving or threading, and laser treatments. Said methods must obviously be repeated at varying intervals, and do not solve the problem permanently.

Pharmacological remedies based on inhibitors of 5-alpha-reductase, ornithine decarboxylase, S-adenosylmethionine decarboxylase, gamma-glutamyl transpeptidase and transglutaminase have also been proposed. See, in particular, U.S. Pat. Nos. 4,885,289, 4,720,489, 5,095,007, 5,096,911 and 5,132,293.

U.S. Pat. No. 5,648,394 discloses a cream formulation of an ornithine decarboxylase inhibitor, alpha-difluoro-ornithine or eflornithine, which is currently used, under the tradename Vaniqa®, for the treatment of hirsutism.

Other formulations of eflornithine are disclosed in US 2003 0523973 and WO 2007/031950.

Though effective, eflornithine presents some drawbacks associated with its high cost and the formulation difficulties, which are illustrated, for example, in US 2003 0523973.

It should also be borne in mind that eflornithine, previously proposed for the treatment of skin tumours and actinic keratosis, is quite a potent medicament and may require a doctor's prescription.

There is consequently a need for formulations that inhibit superfluous hair growth which contain cheap active ingredients easily formulated with no need to use special excipients or absorption promoters, and which are safe to use, with little or no risk of side effects.

DESCRIPTION OF THE INVENTION

It has now been found that capryloyl glycine, a lipoaminoacid conventionally used in various cosmetic compositions for its antimicrobial and pH-regulating properties, effectively combats hirsutism when applied topically.

The present invention therefore relates to topical compositions for the treatment of hirsutism comprising capryloyl glycine as active ingredient, mixed with dermatologically acceptable carriers.

The invention also relates to the cosmetic use of capryloyl glycine to inhibit the growth of hair on the body, especially the face.

The formulations according to the invention can take any form suitable for topical administration, such as gel, cream, foam, ointment, lotion, spray or liquid.

Capryloyl glycine is typically present in the formulations according to the invention in concentrations ranging from 1 to 20% by weight, and preferably from 2.5 to 15% by weight.

The efficacy of the formulations can be further increased by adding other active ingredients, preferably selected from *Curcuma longa* extracts, soy extracts in general and *Gymnema sylvestre* extracts.

The concentrations of said extracts can range from 0.1 to 5% by weight for *Curcuma longa*, 1 to 20% by weight for soy extracts, and 1 to 10% by weight for *Gymnema sylvestre* extracts. The formulations will preferably contain soy extracts in percentages ranging from 5 to 15% by weight.

Suitable dermatological carriers include oil-in-water or water-in-oil emulsions, thickening agents, antifoaming agents, emulsifiers, surfactants, perfumes, polyethylene glycol ethers of alkyl alcohols, and ethylene oxide/propylene oxide copolymers.

Other ornithine decarboxylase inhibitors, S-adenosylmethionine decarboxylase inhibitors, gamma-glutamyl transpeptidase inhibitors or transglutaminase inhibitors can also be added to the formulations if desired. For example, the formulations can include eflornithine, optionally in lower concentrations than those used to date and currently marketed. However, the presence of eflornithine is not necessary to produce the anti-hirsutism effects due to capryloyl glycine, which has proved fully effective even when not combined with other active ingredients.

Said effects are probably due to properties involving inhibition of the enzyme ornithine decarboxylase. However, the usefulness of the invention is in no way dependent on verification of said hypothetical action mechanism.

The invention is illustrated in greater detail in the examples below.

Example 1 purified water 49.7%
lipacide 5% (capryloyl glycine)
propylene glycol 33%
sepigel 3%
cyclopentasiloxane 4%
propyl paraben 0.1%
methyl paraben 0.1%
sodium hydrate to pH 5/5.5
titrated soy extracts 5%

Example 2 lipacide 10% (capryloyl glycine)
propylene glycol 30%
sepigel 3%
cyclopentasiloxane 4%
propyl paraben 0.1%
methyl paraben 0.1%
sodium hydrate to pH 5/5.5
titrated soy extracts 5%
water q.s.

Example 3

Lipacide C8G (capryloyl glycine) 4%
Palmatine supported in 5-micron nylon microbeads and suspended in an oily carrier (Depiline®) 2%
Soya isoflavones 1.5%
Vitamin PP 1.5%

Example 4

The ability of capryloyl glycine to inhibit the growth of superfluous hair was evaluated by the Trichoscan® method (http://trichoscan.com/pages/english/professional-info/reference-values.php). A 10% capryloyl glycine cream proved to have an efficacy comparable to that of eflornithine, reported in Eur. J Dermatol 2008; 18 (1): 65-70.

The invention claimed is:

1. Method of inhibiting growth of superfluous hair on a body in need thereof with a composition consisting of 1 to 20% by weight of capryloyl glycine as active ingredient in admixture with dermatologically acceptable excipients, said method comprising applying said composition to said body.

2. The method according to claim 1, wherein said composition is in the form of gel, cream, foam, ointment, lotion, spray, liquid.

3. The method according to claim 1 to inhibit the growth of hair on the face.

4. A method of treating hirsutism on a body in need thereof with a composition consisting of 1 to 20% by weight of capryloyl glycine as active ingredient in admixture with dermatologically acceptable excipients, said method comprising applying said composition to said body.

5. The method according to claim 4, wherein said composition is in the form of gel, cream, foam, ointment, lotion, spray, liquid.

6. The method according to claim 4, wherein said hirsutism is on the face.

7. The method according to claim 1, wherein the capryloyl glycine is present in an amount from 2.5 to 15% by weight.

8. The method according to claim 4, wherein the capryloyl glycine is present in an amount from 2.5 to 15% by weight.

* * * * *